(12) United States Patent
Swain et al.

(10) Patent No.: US 9,375,202 B2
(45) Date of Patent: Jun. 28, 2016

(54) DEVICE AND METHOD FOR IN VIVO CYTOLOGY ACQUISITION

(71) Applicant: GIVEN IMAGING LTD., Yoqneam (IL)

(72) Inventors: Christopher Paul Swain, London (GB); Charles Alexander Mosse, London (GB); Gavriel J. Iddan, Haifa (IL); Jeremy Pinchas Gerber, Netanya (IL)

(73) Assignee: GIVEN IMAGING LTD., Yoqneam (IL)

( * ) Notice: Subject to any disclaimer, the term of this patent is extended or adjusted under 35 U.S.C. 154(b) by 88 days.

(21) Appl. No.: 13/887,957

(22) Filed: May 6, 2013

(65) Prior Publication Data

US 2013/0296738 A1    Nov. 7, 2013

Related U.S. Application Data

(60) Provisional application No. 61/642,777, filed on May 4, 2012.

(51) Int. Cl.
| | |
|---|---|
| A61B 10/00 | (2006.01) |
| A61B 10/02 | (2006.01) |
| A61B 1/04 | (2006.01) |
| A61B 10/04 | (2006.01) |
| A61B 1/00 | (2006.01) |

(52) U.S. Cl.
CPC ........... *A61B 10/02* (2013.01); *A61B 1/041* (2013.01); *A61B 10/04* (2013.01); *A61B 1/00087* (2013.01); *A61B 10/0275* (2013.01); *A61B 2010/0216* (2013.01)

(58) Field of Classification Search
CPC .... A61B 10/02; A61B 10/0275; A61B 10/04; A61B 1/041; A61B 2010/0216; A61B 1/00087
USPC .......................................................... 600/569
See application file for complete search history.

(56) References Cited

U.S. PATENT DOCUMENTS

| 4,278,077 A | * | 7/1981 | Mizumoto ................... 600/109 |
| 5,343,243 A | | 8/1994 | Maeda |
| 5,604,531 A | | 2/1997 | Iddan et al. |

(Continued)

FOREIGN PATENT DOCUMENTS

| DE | 344 0177 | 6/1986 |
| EP | 1757099 | 2/2007 |

(Continued)

OTHER PUBLICATIONS

International Search Report, issued Mar. 16, 2006, for PCT International Patent Application No. PCT/IL2005/000510.

(Continued)

*Primary Examiner* — Adam J Eiseman
*Assistant Examiner* — Patrick Fernandes
(74) *Attorney, Agent, or Firm* — Pearl Cohen Zedek Latzer Baratz LLP

(57) ABSTRACT

A device, system and method for cytology acquisition which may be performed with a swallowable in vivo device, specifically with a swallowable endoscopy capsule. The swallowable capsule may comprise a rotatable drum, a brush attached onto the drum for brushing against a tissue and acquiring cytology, and a porthole through which the brush may be in contact with the tissue.

15 Claims, 14 Drawing Sheets

(56) References Cited

U.S. PATENT DOCUMENTS

| | | | |
|---|---|---|---|
| 5,993,378 A | 11/1999 | Lemelson | |
| 6,240,312 B1* | 5/2001 | Alfano et al. | 600/476 |
| 7,039,453 B2* | 5/2006 | Mullick et al. | 600/476 |
| 7,192,397 B2 | 3/2007 | Lewkowicz et al. | |
| 7,914,442 B1 | 3/2011 | Gazdzinski | |
| 7,946,979 B2 | 5/2011 | Gilad et al. | |
| 8,084,898 B2 | 12/2011 | Katayama | |
| 2001/0051766 A1 | 12/2001 | Gazdzinski | |
| 2002/0102707 A1 | 8/2002 | Harrow et al. | |
| 2002/0103417 A1 | 8/2002 | Gazdzinski | |
| 2002/0109774 A1 | 8/2002 | Meron et al. | |
| 2003/0023150 A1 | 1/2003 | Yokoi et al. | |
| 2003/0214580 A1 | 11/2003 | Iddan | |
| 2003/0216622 A1 | 11/2003 | Meron et al. | |
| 2004/0176664 A1 | 9/2004 | Iddan | |
| 2005/0272972 A1* | 12/2005 | Iddan | 600/102 |
| 2008/0199065 A1* | 8/2008 | Swain | 382/133 |
| 2009/0143697 A1 | 6/2009 | Tanaka | |
| 2010/0285084 A1* | 11/2010 | Yang et al. | 424/423 |
| 2011/0184235 A1* | 7/2011 | Schostek et al. | 600/109 |
| 2011/0301497 A1 | 12/2011 | Shachar | |

FOREIGN PATENT DOCUMENTS

| | | |
|---|---|---|
| JP | 04-109927 | 4/1992 |
| JP | 1992-144533 | 5/1992 |
| JP | 04-176443 | 6/1992 |
| JP | 06-114037 | 4/1994 |
| JP | 07-111985 | 5/1995 |
| JP | 07-289504 | 11/1995 |
| JP | 2002-286601 | 10/2002 |
| JP | 2003-524448 | 8/2003 |
| JP | 2003-325438 | 11/2003 |
| JP | 2004-016504 | 1/2004 |
| JP | 2004-073887 | 3/2004 |
| JP | 2004-329292 | 11/2004 |
| JP | 2007-537817 | 12/2007 |
| WO | WO 00/44285 | 8/2000 |
| WO | WO 01/65995 | 9/2001 |
| WO | WO 02/26103 | 4/2002 |
| WO | WO 03/090618 | 11/2003 |
| WO | WO 2005/112460 | 11/2005 |
| WO | WO 2005/120325 | 12/2005 |
| WO | WO 2005120325 A2 * | 12/2005 |

OTHER PUBLICATIONS

Supplementary Partial European Search Report for European Application No. EP 05 74 1171, dated Apr. 22, 2009.

Yamashita et al. "Fabrication of Magnetic Microactuators for Cytology Brush Built into Capsule Endoscope." Electronics and Communications in Japan, vol. 98, No. 4, 2015.

* cited by examiner

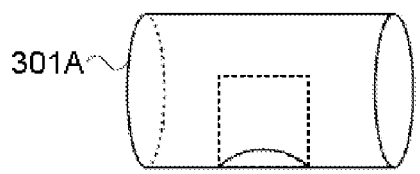
FIG. 3A
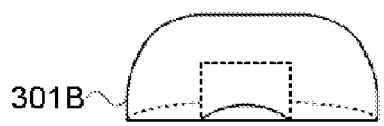
FIG. 3B

FIG. 3C
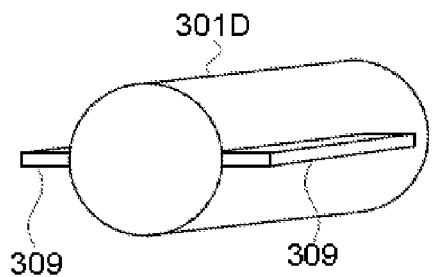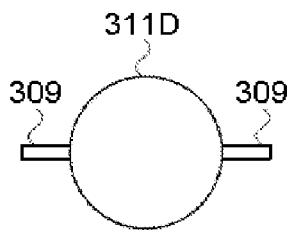
FIG. 3D

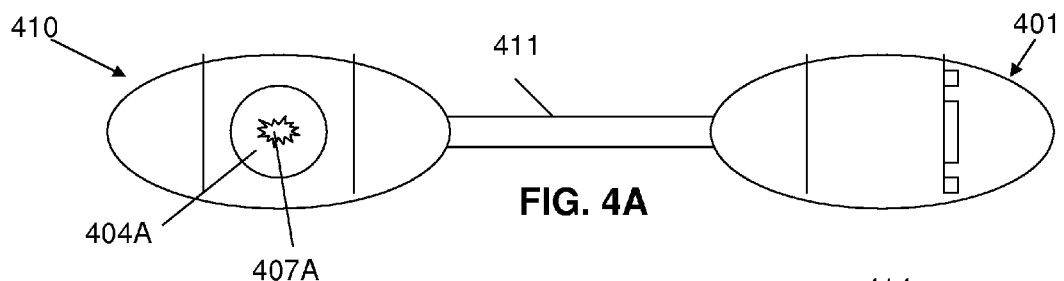
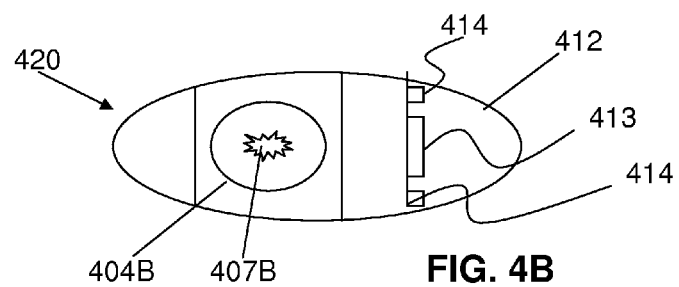
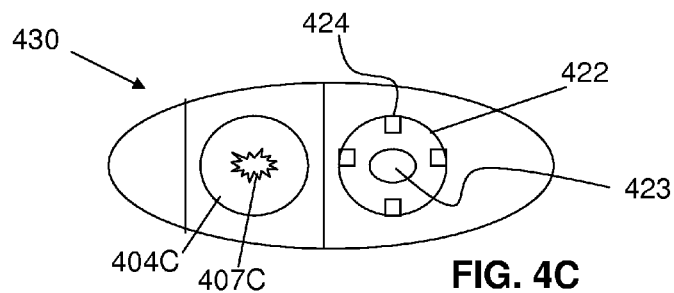
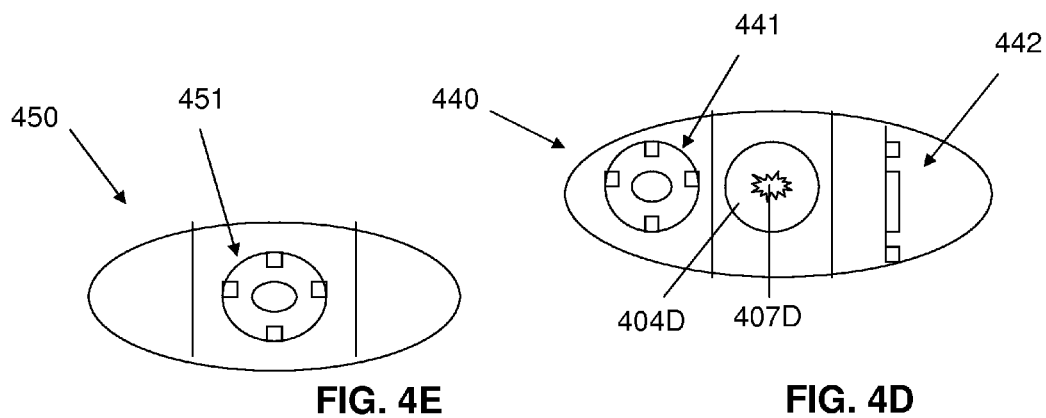

DEVICE AND METHOD FOR IN VIVO CYTOLOGY ACQUISITION

CROSS-REFERENCE TO RELATED APPLICATIONS

This application claims priority from U.S. Provisional Patent Application No. 61/642,777, filed May 4, 2012, which is hereby incorporated by reference in its entity.

FIELD OF THE INVENTION

The present invention relates to cytology acquisition and to cytology acquisition by a swallowable in-vivo device in particular.

BACKGROUND OF THE INVENTION

Examination of cellular tissue acquired through endoscopes, either by brush cytology or biopsy, has become the most common form of acquisition of tissue from the body, specifically from the gastrointestinal (GI) tract, to assess the presence or absence of cancer or diagnose other forms of cancer. As of today, merely imaging the tissue is not enough in order to assess whether or not the tissue is malignant. Cytology and biopsy may assist in providing better diagnosis of the tissue's condition.

Cytology acquisition and biopsy are the most common form of intervention at flexible endoscopy. However, cytology acquisition and biopsy that are performed through endoscopes may be inconvenient to the patient undergoing the endoscopy procedure. Flexible endoscopes, as flexible as they may be, still cause discomfort during insertion into the patient and have the disadvantage of not being able to reach a large portion of the small bowel and some portions of the colon.

There is, therefore, a need for a device that could enable cytology acquisition and biopsy at any location along the GI tract, in a more patient-friendly procedure.

SUMMARY OF THE INVENTION

The present invention provides a device, system and method for cytology acquisition which may be performed with a swallowable in vivo device, specifically with a swallowable endoscopy capsule.

According to some embodiments of the present invention, a swallowable capsule that may perform cytology acquisition or biopsy may be maneuvered to a region of interest. The capsule may typically be maneuvered by magnetic fields; however, other methods of maneuvering may be used.

In some embodiments, the capsule may include at least one controllably openable and closable porthole behind which is located a cytology brush or a porous material. When the porthole is opened, the cytology brush or porous material may contact a surface of the region of interest. The brush cytology or porous material may be moved, for example by being rotated, against the region's surface so that the brush collects cells from that region's surface, or the porous material absorbs body fluids or collects cells, during movement of the brush/porous material.

In some embodiments, the port through which the brush cytology, or porous material, collects cells may be closed, for example, subsequent to cells collection, so that the brush, or porous material, is not contaminated with fluids and particles that flow in-vivo, other than the acquired cells.

According to some embodiments, after the cells acquisition is completed and the porthole is closed so that the cells are not contaminated, the capsule may be released from the force, which is typically magnetic, that holds the capsule near the region of interest. The capsule may then naturally pass through the GI tract and out of the patient. In other embodiments, the capsule may be attached to a delivery device (e.g., wire), which inserts the capsule in-vivo, and, following completion of the procedure of cytology acquisition or biopsy, the capsule may be extracted (e.g., backwards) through the patient's mouth and out of the patient.

The details of one or more embodiments are set forth in the accompanying figures and the description below. Other features, objects and advantages of the described techniques will be apparent from the description and drawings and from the claims.

BRIEF DESCRIPTION OF THE DRAWINGS

The above and other objects and advantages of the invention will be apparent upon consideration of the following detailed description, taken in conjunction with the accompanying drawings, in which the reference characters refer to like parts throughout and in which:

FIGS. 3A-3D illustrate schematic side views and cross sections of cytology capsules in accordance with several embodiments of the present invention;

FIGS. 4A-4E illustrate schematic side views of cytology capsules in accordance with several embodiments of the present invention;

Figure 1:
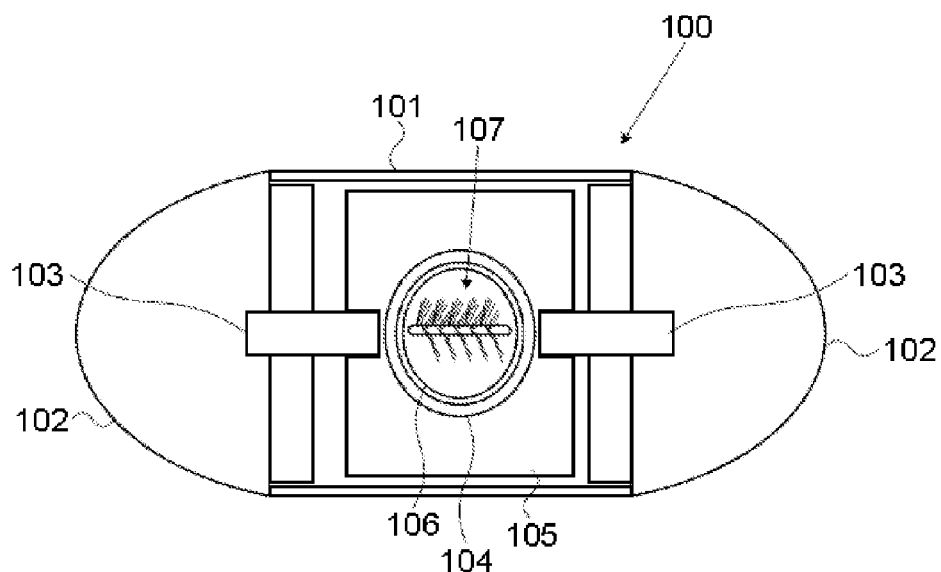
FIG. 1 illustrates a schematic upper view of a cytology capsule in accordance with one embodiment of the present invention.

It will be appreciated that, for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF EMBODIMENTS OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures and components have not been described in detail so as not to obscure the present invention.

Embodiments of the present invention provide devices and methods for cytology acquisition. Typically, the in-vivo device is a swallowable autonomous capsule, which may comprise or be equipped with a mechanism for performing cytology or biopsy acquisition. By "autonomous capsule" is generally meant a capsule capable of being moved in the GI system without using threads, strings, wires, cables, etc., but by peristalsis or by wireless maneuvering.

Figure 7:
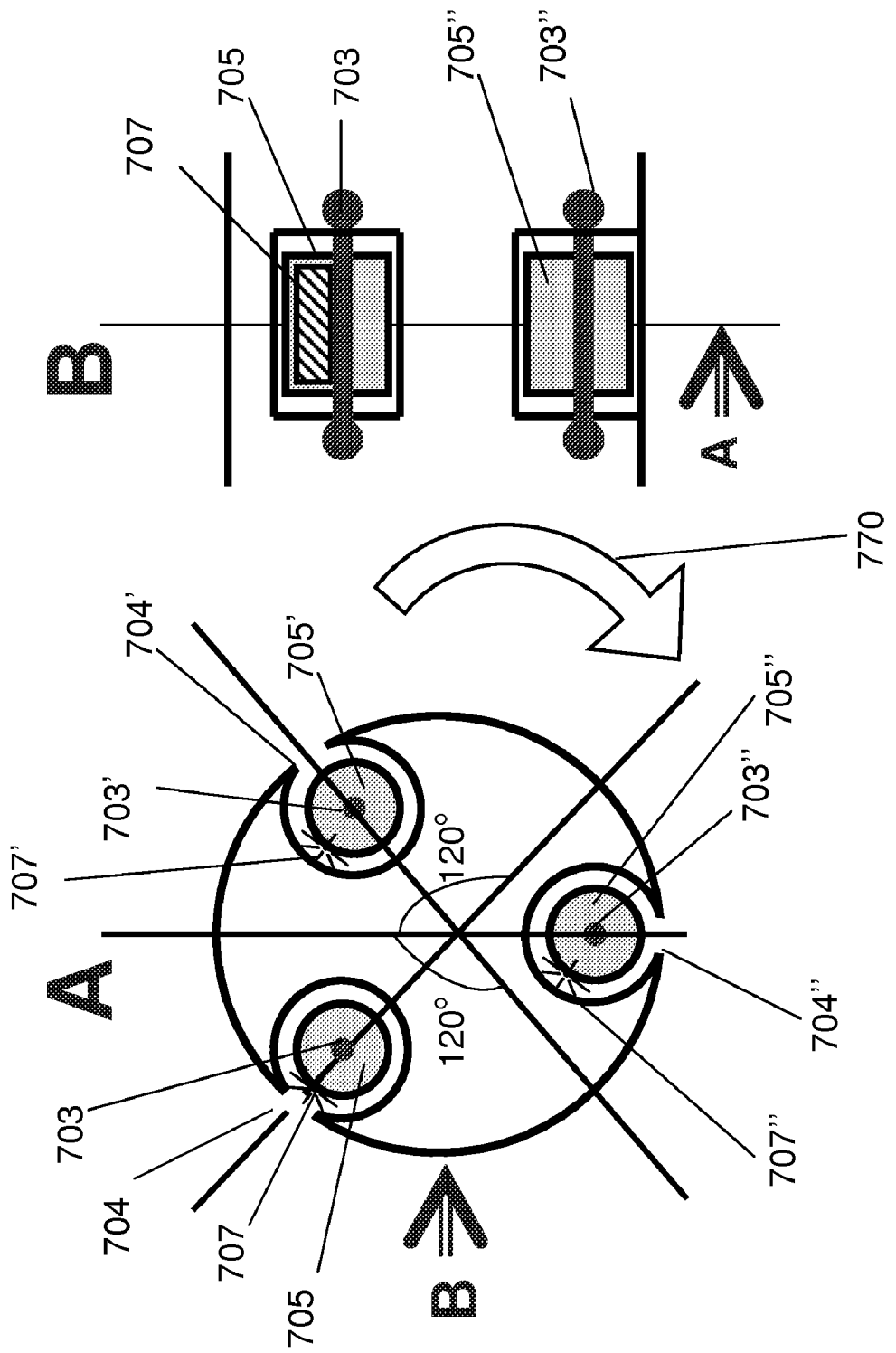
FIG. 7 illustrates a schematic cross-section of a sampling wheel of a cytology capsule in accordance with one embodiment of the present invention.
Figure 8:
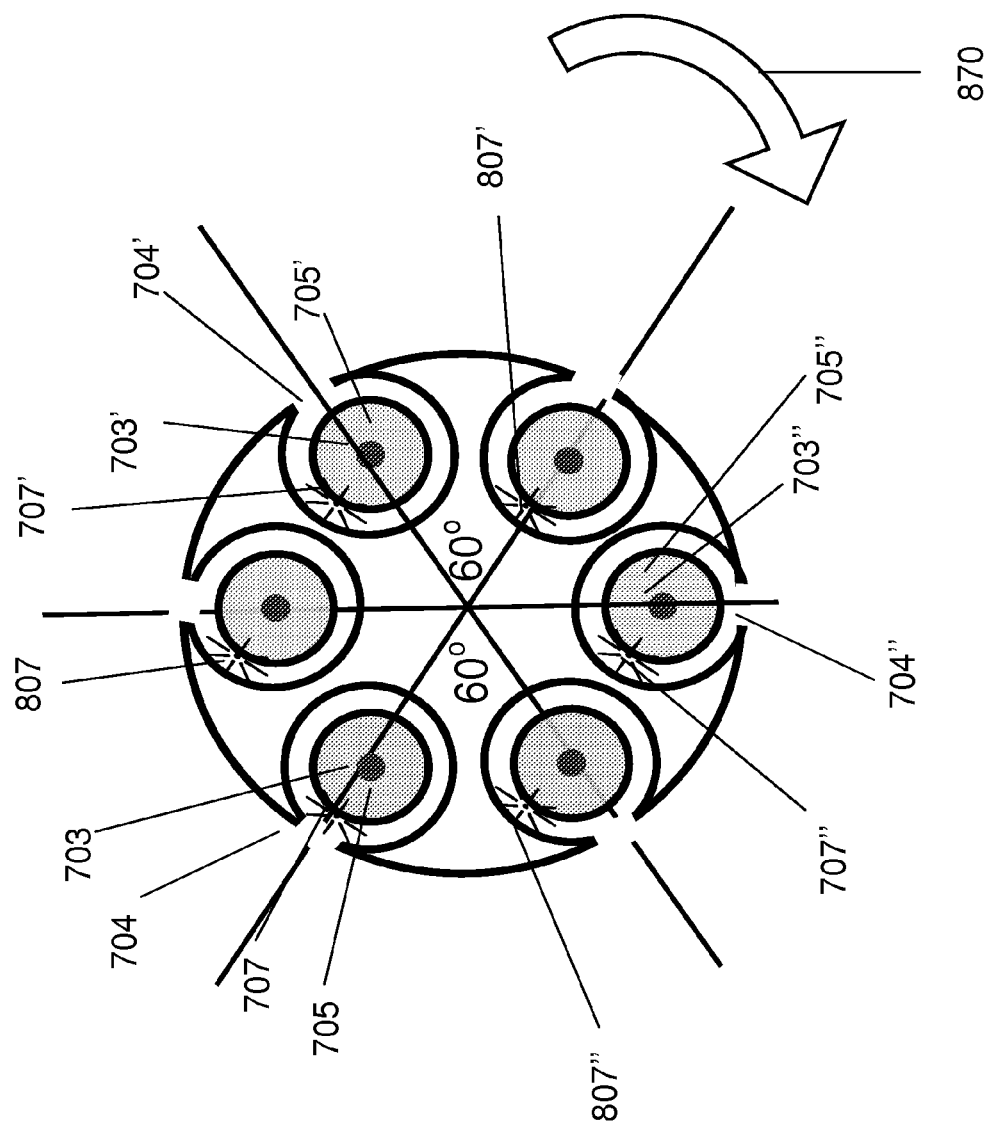
FIG. 8 illustrates a schematic cross-section of a sampling wheel of a cytology capsule in accordance with another embodiment of the present invention.
Figure 12:
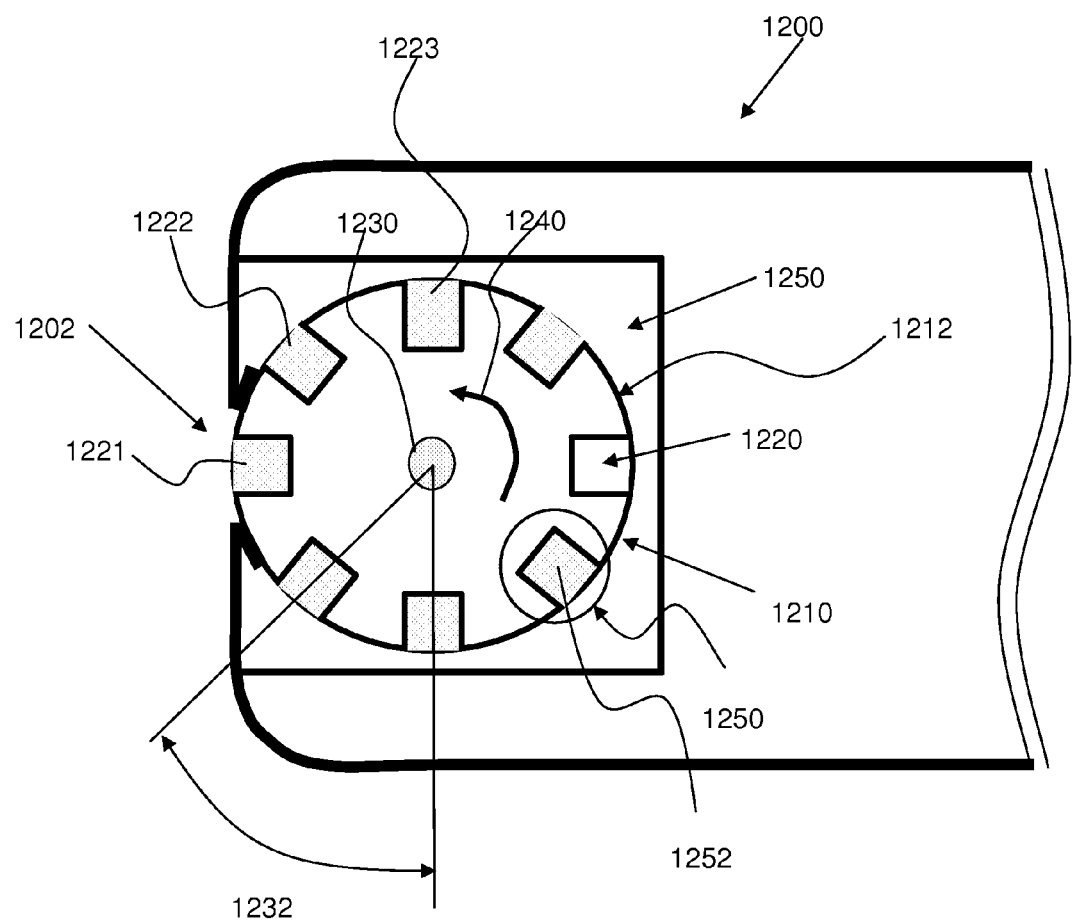
FIG. 12 shows a partial cross-section view of a cytology capsule according to another example embodiment.

By "capsule" is generally meant a diagnostic or therapeutic device which is small enough to be swallowed, and which may be encased, for example, in a cylindrical container that may contain an electronic circuit and/or optical components and/or surgery tools, and/or a moving mechanism for operating a tool internally (inside the device) or externally. According to the present invention, such a capsule may also be capable of harvesting tissue cells or tissue specimen (e.g., for performing biopsy or cytology) by using a sampling wheel, and holding the cellular/tissue material usually until the capsule has left the body either naturally (through excretion) or by being retrieved, for example, through the mouth by using, for example, a string or a wire. The capsule may be designed such that the cells/tissue sample(s) harvested by the sampling wheel and momentarily stored in the capsule can be extracted easily for analysis (e.g., by a pathologist) after the capsule is retrieved either through the mouth or through the anus. The sampling wheel may include one or more sampling cavities, each sampling cavity may include or contain a brush, for example as shown in FIGS. 7 and 8, or a porous material (e.g., sponge), for example as shown in FIG. 12. Each sampling cavity may have a porthole through which the brush can scrape tissues, or the porous material can absorb a body fluid or scrape tissues.

A sampling wheel may be static in the sense that it does not have to be rotated in order for a sampling cavity (and a cells/tissue sampling means which it may contain, be it, for example, a brush or a porous material) and a porthole window (through which sampling may take place) to be aligned, because each sampling cavity (and thus each sampling means) typically has its own porthole. A static sampling wheel is shown, for example, in FIGS. 7 and 8, in which the sampling means is a brush. A static sampling wheel may be thought of as a sampling wheel that includes on-board portholes. A sampling wheel may be dynamic in the sense that it has to be rotated in order to align a sampling cavity and a porthole, because the sampling cavities of the sampling wheel use one, common, porthole that is stationary, and the sampling cavities can be used only one sampling cavity at a time. A dynamic sampling wheel may be thought of as a sampling wheel that does not include an on-board porthole but rather uses a porthole window in the capsule's shell (A dynamic sampling wheel is shown, for example, in FIGS. 11 and 12.

Although using an autonomous cytology capsule has advantageous, for example such a capsule may take cells/tissue samples from inside the GI system or other parts of the body without patient discomfort, the capsule may be connected to a thread, cable or wire by which it may be pulled out, for example, through the mouth. That is, the capsule may be swallowed with a thread attached thereto, and used, for example, to 'brush' the cardio-esophageal junction when it reaches the mucosal junction between the stomach and the esophagus—usually between 35-40 centimeters from the teeth—and then withdrawn to look for evidence of Barratt's tissue or cancer. The capsule may include an image sensor, but knowing the length of the esophagus may render the image sensor unnecessary. A capsule without an image sensor may take random specimens from the small intestine looking for diffuse abnormalities such as celiac disease in the proximal intestine, Crohn's disease in the lower small intestine, colitis in the colon, etc. The sampling wheel of the cytology capsule may be operated (e.g., rotated) in various ways as described herein (e.g., by using external magnet, external electromagnetic field, spring, or motor), though other methods for operating the sampling wheel may be used.

Figure 2:
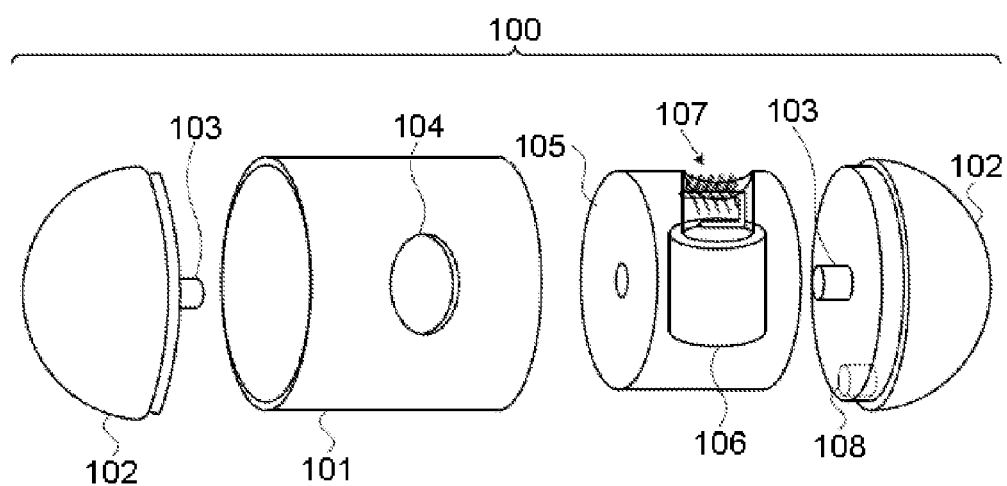
FIG. 2 illustrates a schematic exploded view of a cytology capsule in accordance with one embodiment of the present invention.

Reference is now made to FIGS. 1 and 2, which illustrate a schematic upper view of a cytology capsule 100 and a schematic exploded view of cytology capsule 100, respectively, in accordance with an embodiment of the present invention. In some embodiments, cytology capsule 100 may be suitable for acquiring cytology in tubular regions of the GI system. Capsule 100 may comprise a shell 101 attached to two ends, or domes, 102 (one on each side of shell 101), each typically shaped as a cone. In some embodiments, capsule 100 may comprise a drum-like sampling wheel 105 (or "drum", for short). Drum 105 may be rotated around the longitudinal axis of capsule 100. Capsule 100 may comprise one or two spindles 103 around which drum 105 may rotate. Drum 105 may have attached to it a cytology brush 107 which, when moved against a tissue surface, may acquire cells from the (scraped) tissue. Capsule's shell 101 may comprise an opening, window or porthole 104 through which the cytology brush 107 may contact and scrape the tissue. Typically, the cytology brush 107 attached to drum 105 may be rotated around the longitudinal axis of capsule 100, along which spindles 103 are mounted.

According to embodiments of the invention, following insertion of capsule 100 into the patient's GI tract, capsule 100 may be magnetically maneuvered to a region of interest. Capsule 100 may, therefore, comprise a magnetic element (the capsule's maneuvering magnet is not shown) which may enable capsule 100 to be manipulated (e.g., steered) by an external magnet or by an external magnetic field to a region of interest, from the tissue of which the physician might want to acquire cells for later examination when the capsule exits from within the patient. Once the external magnet is distanced away from the patient's body, or the external magnetic field is deactivated or shut down, capsule 100 may continue to move in the GI system using peristaltic force.

Capsule 100 may comprise an internal magnet 106 positioned within drum 105, which may enable drum 105 to be manipulated by an external magnet (the external magnet is not shown), such as to rotate drum 105 and cytology brush 107, such that porthole 104 and cytology brush 107 are in alignment when capsule 100 is in contact with the surrounding tissue and cells acquisition is required. In the absence of an external magnetic field, magnet 106 and a biasing magnet 108 may be so arranged so that, in a resting position, cytology brush 107 is not in alignment with the porthole 104, but rather a certain degrees, for example, 180 degrees, away from the porthole 104, and porthole 104 may be effectively closed by drum 105. By "resting position" is meant a non-sampling position, or a position in which no cells' harvesting/acquiring is performed.

Once the region of interest is reached, a sufficiently powerful external magnet (the external magnet is not shown) may be brought up or in proximity to the patient and maneuvered (e.g., rotated), in order to cause drum 105 to rotate so that brush 107 passes over and is in alignment with porthole 104. Once brush 107 has passed across porthole 104 and brushes against the tissue at the region of interest, the external magnet may be withdrawn and distanced away from the patient to allow biasing magnet 108 to "park", or lock, the brush 107 away from porthole 104. For example, the brush 107 may be angularly displaced or moved, for example 180 degrees, away from porthole 104. In some embodiments, if brush 107 is parked away from porthole 104, drum 105 may effectively close porthole 104, for example to prevent contaminants from entering cytology capsule 100 (e.g., drum 105), and/or harvested cells from leaking out. In some applications the cytology capsule may reside in the GI system for hours, during which time harvested cells (or harvested tissue sample(s)) may deteriorate. In order to prevent deterioration, degradation or decaying of harvested cells or harvested tissue samples, the cytology capsule may include a container for storing a cell/tissue preservative, a material that has a desiccating and antibacterial effect, a Polyethylene glycol, an ethyl alcohol, etc. An injection or spraying mechanism may controllably be used to inject or to spray the cell/tissue preservative onto the harvested cells or tissue sample. In some embodiments, magnet 106 may be made of different magnetic materials or may be made of materials (e.g., iron) that are attractable to or can interact with magnets.

In some embodiments, cytology brush 107 may be used by rubbing the brush on or against the target lesion. Brush 107 may be removed from cytology capsule 100 after capsule 100 exits the patient's body. Brush 107 may then be stroked across a microscope slide to smear cells, preferably evenly across the slide so that individual cells may be examined. The microscope slide may then be fixed with a fixative and preservative, and may be stained so that the intracellular components thereon may be seen. Examples of cytology brushes that may be used are COOK™ cytology brushes, and Curaprox Interdental Brushes Regular White. In some embodiments, cytology capsule 100 may comprise a curved or flat surface on a plate that may be pulled out with the cells on it and then sent to the pathologist for analysis. The plate, which may be in or external to drum 105, may be regarded as a cells collector. The plate, or cells collector, may be detachably connected, for example, to drum 105 to facilitate easy pull-out removal thereof.

According to some embodiments, biasing magnet 108 may be replaced by a non-magnetic element (e.g., spring, spring coil, etc.). This may allow magnets to be placed in capsule's end(s) 102 in such a way that the magnets may facilitate external maneuvering of cytology capsule 100 within the GI tract while drum 105 may be activated by rotating the external magnet. That is, the external magnet may have two functions: maneuvering capsule 100 to regions of interest, and rotating drum 105 so that brush 107 may contact the tissue and acquire cells through porthole 104.

Reference is now made to FIGS. 3A-3D, which illustrate schematic side views and cross sections of cytology capsules in accordance with several embodiments of the present invention. In some embodiments, the body of cylindrically shaped capsules such as capsule 301A, which has a round cross-section 311A (shown in FIG. 3A) may rotate with the drum so that the brush may not pass across the porthole, and may not be able to contact the tissue and brush against it for cells acquisition. It is desirable that the drum be rotated relative to the capsule body. Several ways are possible to achieve this, for example, by changing the capsule's shape from a cylindrically-shaped capsule to an elliptically-shaped capsule 301B, which also has a D-shaped cross-section 311B (shown in FIG. 3B). In some embodiments, when an external magnet (not shown) is applied in close proximity to the patient, the capsule may tend to orientate itself so that the flat portion of the "D" shape is closest to the external magnet. In some embodiments, the porthole may be positioned at the flat back of the capsule. In such embodiments, it may be possible to use an external magnet (not shown) to position the porthole against the region of interest, so that tissue cells may be collected by the brush at a particular orientation with respect to the tubular GI section the cytology capsule is currently in. Other shapes that would resist the capsule body turning are an eye-shaped or "turtle" shaped capsule 301C (shown in FIG. 3C) or a capsule comprising fins, as capsule 301D (shown in FIG. 3D), or other non cylindrically shaped capsules. In some embodiments, capsule 301D may comprise extendable fins. In this embodiment, when the capsule 301D is swallowed by the patient, the fins are folded around the capsule, creating a cylindrically shaped capsule. However, when the capsule reaches a region of interest, the fins may extend outward from the cylindrically shaped capsule, thereby creating "stoppers" that may stop the capsule's outer body from turning along with the inner drum.

According to some embodiments, rather than a cylindrical drum 105 (as shown in FIG. 2), a spherically-shaped holder or an ellipsoidally-shaped holder for brush 107 and (brush) magnet 106 (like the ball in a ball point pen) may be used. This spherical brush and magnet holder may be mounted or built into the dome of the capsule 100.

Reference is now made to FIGS. 4A-4E which illustrate schematic side views of cytology capsules in accordance with several embodiments of the present invention. FIG. 4A illustrates a schematic side view of a cytology capsule 410 connected to an imaging capsule 401 through a connector 411. In some embodiments, connector 411 may be flexible while, in other embodiments, it may be rigid. Cytology capsule 410 may comprise a porthole 404A through which cytology brush 407A may collect cells from a region of interest. While cytology capsule 410 collects the cells, imaging capsule 401 may acquire images of the lumen. Thus, two operations may be done at once—cytology acquisition and image acquisition, both of which may provide information on the patient's condition.

With the increased miniaturisation of electronics it may be possible to incorporate both functionalities (cytology and imaging) into one capsule, as illustrated in FIG. 4B. Capsule 420 may comprise a porthole 404B through which brush 407B may acquire tissue cells, while further comprising an imaging end 412, through which in-vivo images may be acquired. Imaging end 412 may include, for example, an image sensor 413 and an illumination source 414. Capsule 420 may also comprise a control circuit, for example for controlling operation of image sensor 413 and illumination source 414, and for processing images captured by image sensor 413 and/or data related to captured images and/or data related to, or derived, resulting or originating from other activities of, or processes executed by, capsule 420. In other embodiments, for example as illustrated in FIG. 4C, imaging system 422 (which may comprise an imager 423, illumination sources 424 and an optical system (not shown)) may be located such that it acquires images through the optically transparent side of capsule 430 and not from the front end of the capsule, as illustrated in FIG. 4B. In such embodiments, brush 407C may acquire cells through porthole 404C from a region of interest, while imaging system 422 may image that same region of interest. In some embodiments, it might be preferable to have a transparent partition between the imaging system and the cytology system, so that the imaging system may monitor the operation of the rotating drum or the brush, either from inside or outside the capsule.

In other embodiments, as illustrated in FIG. 4D, capsule 440 may comprise at least two imaging systems. In addition to brush 407D, capsule 440 may comprise a first imaging system 441, which may acquire images through the side of the capsule 440, e.g., it may acquire images of the region of interest from which cytology is acquired. Capsule 440 may further comprise a second imaging system 442, which may be located at one of the ends of capsule 440, for example at the capsule's end opposite the end accommodating the first imaging system. Imaging system 442 may image the in-vivo lumen at a direction parallel to the direction of movement of the capsule (when no external magnet is applied). Imaging systems 441 and 442 may be similar to imaging system 412 or to imaging system 422.

In yet other embodiments, as illustrated in FIG. 4E, capsule 450 may comprise a cytology brush (not shown) and an imaging system 451, both mounted on the same/common drum in order to occupy less space in capsule 450.

Figure 5:
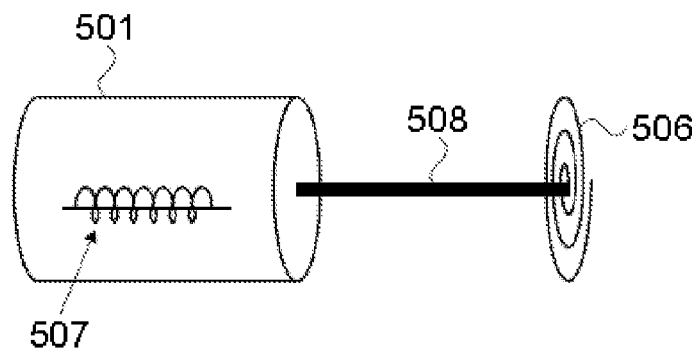
FIG. 5 schematically illustrates part of a cytology capsule in accordance with one embodiment of the present invention.

Reference is now made to FIG. 5, which schematically illustrates part of a cytology capsule in accordance with one embodiment of the present invention. In some embodiments, it may be possible to replace the magnet in the drum (e.g., magnet 106 of FIG. 2) by a spring such as spring 506, for example a torsion spring or a spiral clockwork spring, that may rotate the drum (e.g., drum 501) or bias the drum against rotation. Spring 506 may be controllably triggered by, for example, a solenoid that may be operated wirelessly, for example by using an RF-activated switch. This may mean that the capsule may be magnetically maneuvered without the cytology function being affected or interfered with. Spring 506 may be initially wound so that when the capsule arrives at the site where cells need to be harvested/acquired, the potential energy stored in spring 506 may be controllably used to rotate drum 105 one or more revolutions, with brush 507 passing a porthole similar to, for example, porthole 104), during each revolution. Alternatively, spring 506 may be wound so that drum 501 may be rotated only partially, with only part of brush 507 passing the porthole (e.g., porthole 104) each time. The energy stored in spring 506 may be controllably released in portions, to facilitate cells' acquisition from different locations in the GI tract. Each energy portion, which is released from spring 506, may rotate drum 501 at least part of a full revolution. Each individual or partial rotation may be separately triggered, where each trigger releases an energy portion. The capsule may include a control unit for locking drum 501 when no cells collection is not required, and for unlocking drum 501 when cells collection is required.

According to other embodiments, a cytology capsule with a spring activated brush does not include magnets. In such embodiments, an external magnet may activate the mechanism that triggers/operates the energy-loaded spring (e.g., spring 506). Alternative triggering mechanisms may comprise an external RF link.

According to some embodiments, it may be necessary to apply, for example, onto the drum, some form of fixative in order to prevent the acquired cells from degrading within the capsule whilst the capsule passes through the GI tract after their acquisition. Also it may be possible to arrange the cytology so that harvested/acquired cells can be easily transferred onto a slide. Spring 506 may be connected to drum 501 by a rod 508 through which spring 506 can transfer a torque force to drum 501.

Figure 6A:
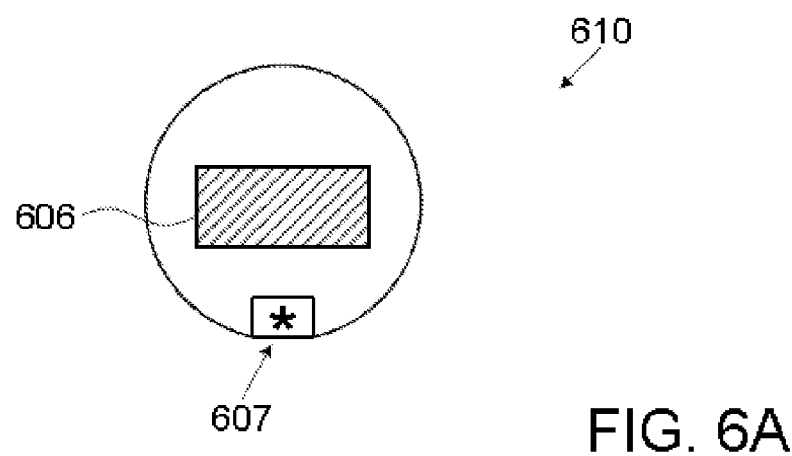
FIGS. 6A-6B illustrate schematic cross-sections of a cytology capsule in accordance with two embodiments of the present invention.
Figure 6B:
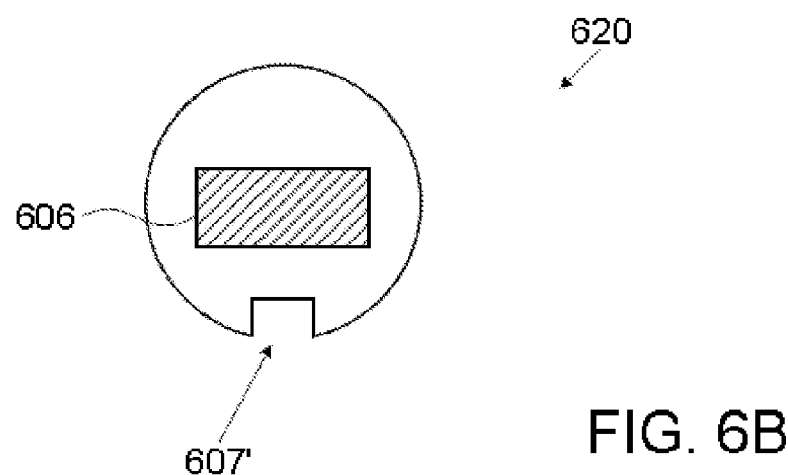

Reference is now made to FIGS. 6A-6B, which illustrate schematic cross-sections of a cytology capsule in accordance with two embodiments of the present invention. FIG. 6A illustrates a cross-section of a cytology capsule which comprises a cytology brush 607. The cytology capsule illustrated in FIG. 6A may be similar to any of cytology capsules 100, 301A-D, 410, 420, 430, 440 or 450 as mentioned herein, i.e., wherein the capsule comprises a magnet 606 attached to, or associated with, a cytology brush for collecting cells from a region of interest. According to all of the above mentioned capsules, the magnet within the capsule may be manipulated by an external magnet, such that when the external magnet rotates (the external magnet is not shown), drum 610, and therefore brush 607, rotates with it or as a result of its rotation. However, the same mechanism may be used to take biopsies when brush 607 is replaced by a cutting edge or knife 607', as illustrated in FIG. 6B. In some embodiments, when drum 620 rotates (e.g., as a result of a rotation of magnet 606 by an external magnet), instead of brush 607 contacting tissue and collecting cells, knife 607' may contact the tissue through a porthole and may cut a piece of the tissue, i.e., a biopsy may be acquired. When drum 620 is further rotated, the harvested piece of tissue may be retained within the capsule until after the capsule exits the patient's body. A receiver receiving signals from the cytology capsule may use the signals to detect the time at which the capsule is excreted naturally out of the body. For example, if the capsule transmits images, images can be used to detect the capsule excretion time because ex-vivo environment is conspicuously visually different than in-vivo environment. The receiver may, then, indicate, for example, to the patient, that the capsule has exited his body.

The acquired/harvested cells (or piece of tissue, when a biopsy is acquired) may be analyzed in order to asses the patient's condition. Therefore, it is necessary that the capsule be safely retrieved in order to extract the harvested cells or tissue sample(s). In some embodiments, retrieval of the capsule may be achieved using a net over the lavatory or by using a magnet on a stick that may be inserted into the lavatory and attract the capsule to it. According to other embodiments, the capsule may be swallowed while attached to a thread or string, in order to increase the number and improve views of, for example, the cardio-esophageal junction. A threaded capsule that comprises cytology brush may be easily retrieved through the patient's mouth and the cytology may be examined by a pathologist.

Figure 9:
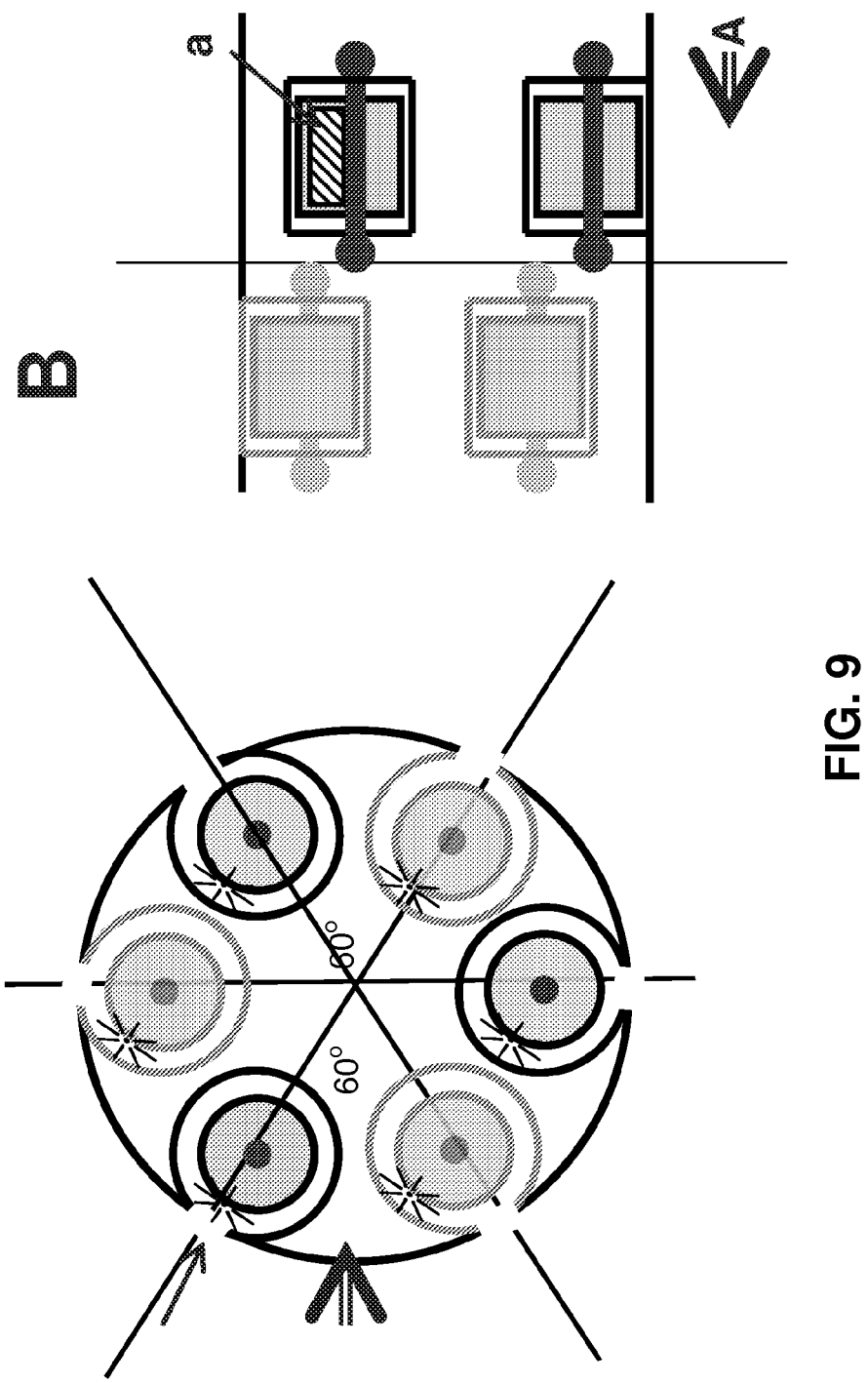
FIG. 9 illustrates a schematic cross-section of a sampling wheel of a cytology capsule in accordance with yet another embodiment of the present invention.

Reference is now made to FIGS. 7-9 which illustrate schematic cross-sections of cytology capsules in accordance with three embodiments of the present invention. The cytology capsules illustrated in FIGS. 7-9 comprise multiple sampling cavities, each sampling cavity having a porthole and a cytology brush carrying drum.

FIG. 7 illustrates a cross-section of a sampling wheel of a cytology capsule that comprises three sampling cavities, each sampling cavity containing a drum and a brush that is connected to the drum and rotatable through rotation of the drum, and a porthole through which the brush can scrape a tissue while the respective drum is rotated. Referring to FIG. 7, the sampling cavities have portholes 704, 704' and 704", each sampling cavity having one porthole. Portholes 704, 704' and 704" may be circumferentially positioned along the sampling wheel, or circumferentially positioned along the body of cytology capsule, at an angle of 120 degrees from one another along the circumference of the capsule. The capsule (e.g., the capsule's sampling wheel) may comprise three drums 705, 705' and 705" that may be rotated about spindles 703, 703', and 703", respectively, against portholes 704, 704' and 704", respectively. In some embodiments, each drum may be located behind a respective porthole, such that drum 705 is located behind porthole 704, drum 705' is located behind porthole 704', and drum 705" is located behind porthole 704". In some embodiments, every drum may have an attached cytology brush, such that brushes 707, 707' and 707" are attached onto drums 705, 705' and 705", respectively. In some embodiments, the brushes are attached onto their respective drums such that when the drums rotate, at least one brush is placed in front of (i.e., it is aligned with) its respective porthole at any time. This ensures that at any given time, there may be a cytology brush exposed to, and collecting cells from, the surrounding tissue. In some embodiments, rotating an external magnet may cause simultaneous rotation of all three drums (each drum typically comprising a magnet) at same speed and orientation. This method may be advantageous for cytology acquisition in the esophagus, where the esophagus surrounds and touches the capsule from all sides, such that every porthole may be in contact with esophageal tissue and three cytology samples may be acquired at once. The angular orientation of the cytology capsule may change, as shown at 770.

Reference is now made to FIG. 8, which illustrates a schematic cross-section of a sampling wheel of a cytology capsule in accordance with another embodiment of the present invention. The capsule in FIG. 8 comprises six sampling cavities, each sampling cavity containing a drum and a brush that is connected to the drum and rotatable through rotation of the drum, and a porthole through which the brush can scrape a tissue while the respective drum is rotated. Referring to FIG. 8, the sampling cavities have cytology brushes 707, 807, 707', 807', 707" and 807", which may be circumferentially located at an angle of 60 degrees from one another along the circumference of the capsule/sampling wheel. In some embodiments, the brushes may be positioned and operated such that there will always be a cytology brush exposed to surrounding tissue at any given time. For example, cytology brush 707 is shown exposed to the outer environment through porthole 704, while the other brushes are at various stages of rotation in the respective sampling cavities. That is, if all six drums are rotated at the same time and at the same speed, brush 807" will be the next brush to face its porthole, then brush 707", then brush 807', then brush 707', then brush 807. Every brush that acquires cells or a tissue piece, when further rotated along with its respective drum, may be positioned such that it is contained within the capsule, as farther away from its respective porthole as possible, in order to avoid cells contamination or leakage. The angular orientation of the cytology capsule may change, as shown at 870.

FIG. 9 illustrates another embodiment where a cytology capsule comprises six cytology brushes, as illustrated in FIG. 8. However, unlike the capsule in FIG. 8 wherein all six brushes are located along the same transverse or longitudinal axis, in FIG. 9 the brushes are located along two different transverse or longitudinal axes. Other numbers of transverse axes along which the cytology brushes may be located at are possible. According to some embodiments, at any one time, there will always be a cytology brush collecting a sample from the surrounding tissue.

Figure 10:
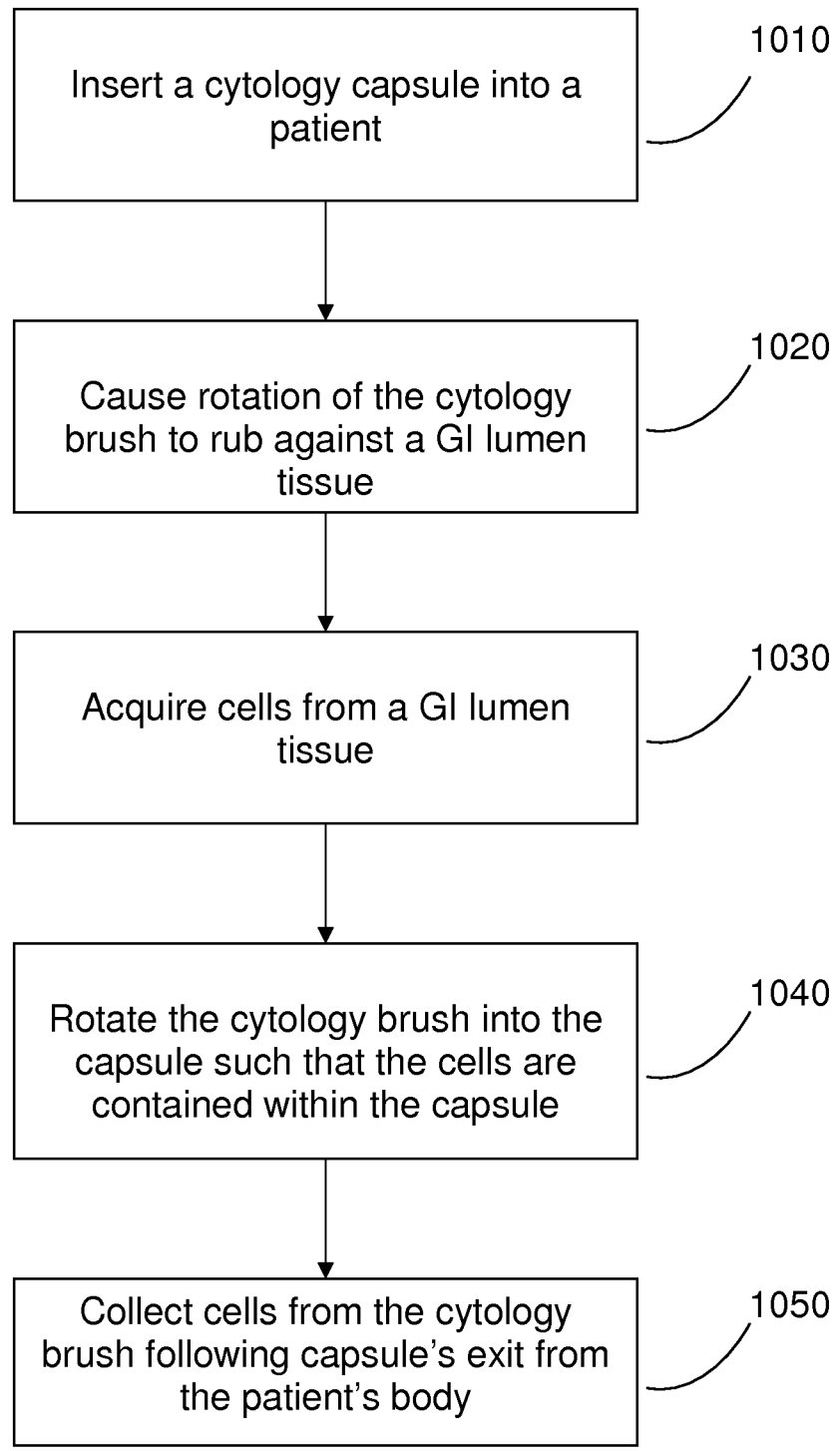
FIG. 10 depicts a method for performing cytology with a cytology capsule in accordance with one embodiment of the present invention.

Reference is now made to FIG. 10, which depicts a method for harvesting cells or a piece of a tissue with a cytology capsule in accordance with one embodiment of the present invention. The method may comprise inserting, at step 1010, into a patient a cytology capsule. The method may further comprise causing, at step 1020, rotation of the cytology brush to scrape/rub against a GI lumen tissue, and thus acquiring, at step 1030, cells, or tissue piece, from a GI lumen tissue. In some embodiments, causing rotation of the brush may be done by rotating an external magnet which may rotate an internal magnet that is attached to the drum and thus to the brush. In some embodiments, the method may further comprise rotating, at step 1040, the cytology brush into the capsule such that the cells are contained within the capsule. The method may further comprise collecting, at step 1050, cells from the cytology brush following capsule's exit from the patient.

Figure 11:
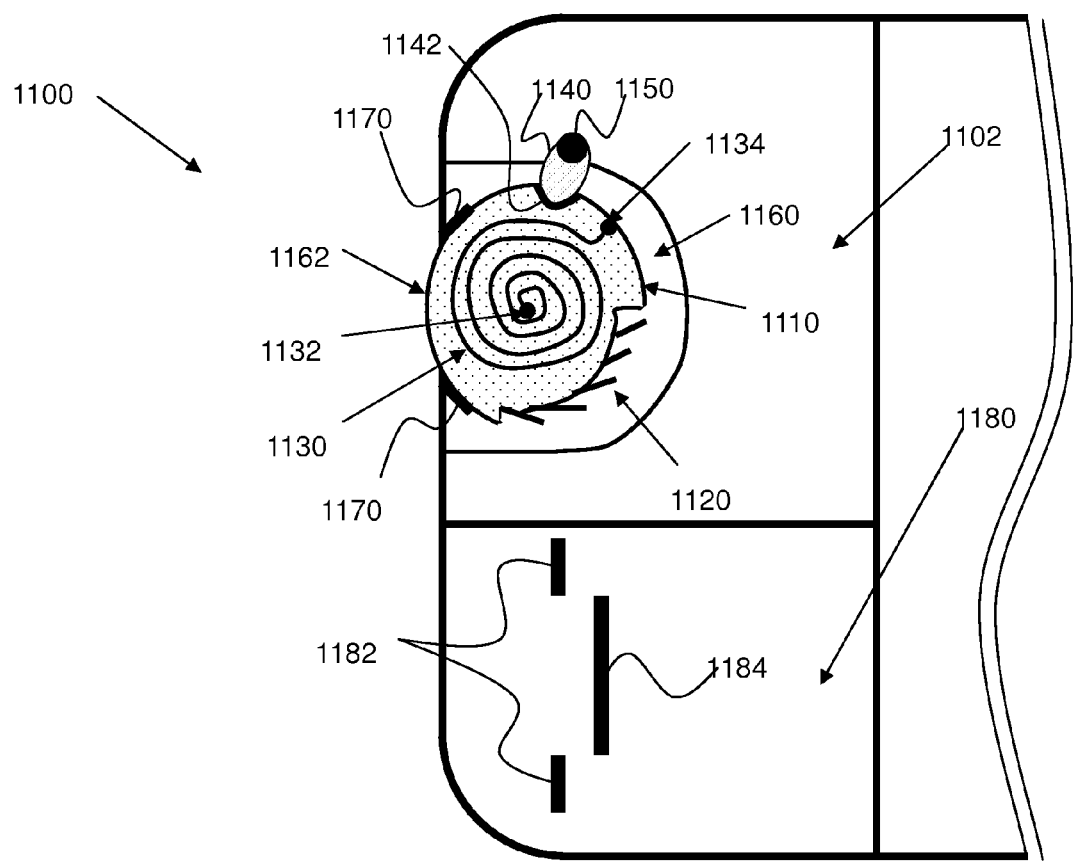
FIG. 11 shows a partial cross-section view of a spring-driven brush-carrying drum according to an example embodiment.

FIG. 11 shows a partial cross-section view of a spring-driven brush carrying drum according to an example embodiment. Cytology capsule 1100 may include a cytology part, section, or compartment, 1102 and an imaging part, section, or compartment, 1180. Cytology section 1102 may include a rotatable (dynamic) sampling wheel 1110, a cytology brush 1120, a spring 1130, a cam 1140 operable about a controllably rotatable hinge 1150, a leak proof chamber 1160, which is sealed by a sealing frame or gasket 1170. The terms "drum" and "sampling wheel" are used herein interchangeably. One end of spring 1130 may be connected to a rod 1132 which is connected to sampling wheel 1110. Rod 1132 is aligned with, and servers as, a rotation axis of sampling wheel 1110. The other end of spring 1130 may be connected to sampling wheel 1110, for example by a peripheral pin 1134 through which spring 1130 may transfer a rotation force to sampling wheel 1110 while spring 1130 is decompressing. Pin 1134 is referred to herein as a "peripheral pin" because it has to be decentred with respect to (rotation) rod 1132 to facilitate application of a rotation force on sampling wheel 1110.

In general, device 1100 may be in a non-harvesting mode or in a harvesting mode. In the non-harvesting mode brush 1120 may be (concealed) in chamber 1160, spring 1130 may be fully compressed to store potential energy, and sampling wheel 1110 may be locked by cam 1140 to inhibit rotation thereof. In addition, in the non-harvesting mode chamber 1160 may be tightly sealed by an impervious protruding part 1162 of the sampling wheel 1110. Sampling wheel 1110 may be retained in position by cam 1140 that may sit in a retaining recess 1142 in sampling wheel 1110. When cells harvesting is required, the mode of capsule 1100 can controllably be changed from non-harvesting to harvesting. In harvesting mode, rotatable hinge 1150 may be caused (e.g., by an actuating mechanism which is not shown in FIG. 11) to rotate a certain amount of degrees (e.g., 30 degrees) to cause cam 1140 to exit (i.e., to release it from) recess 1142 in sampling wheel 1110, to thereby unlock sampling wheel 1110 and enable it to rotate about rotation rod 1132. Unlocking sampling wheel 1110 may enable spring 1130 to release at least some of its stored energy, to thereby rotate sampling wheel 1110 (by pushing peripheral pin 1134).

Sampling wheel 1110 may have multiple retaining recesses similar to retaining recess 1142, and all the retaining recesses may be circumferentially located on the sampling wheel 1110. The retaining recesses may be equidistantly located on sampling wheel 1110, though other arrangements or setups can be used. Cam 1140 may be controlled such that sampling wheel 1110 rotates a certain amount of degrees (a certain angle) at a time (e.g., during each activation of cam 1140), from one retaining recess to another. Sampling wheel 1110 may, but it does not have to, turn the same angle each time cam 1140 is activated. The amount of degrees rotated by sampling wheel 1110 each time generally depends on several parameters, for example the number of the circumferential retaining recesses and their angular arrangement on the circumference of sampling wheel 1110, and these parameters may change according to application. When sampling wheel is unlocked, brush 1120, when exposed to the porthole window of capsule 1100, may scrape cells and may, by rotating sampling wheel 1110 further, discard of them in leak proof chamber 1160. Capsule 1100 may include a motor, for example an electrical motor, for controllably rotating sampling wheel 1110. Such a motor may obviate the need for spring 1130 and cam 1140.

Imaging part, section, or compartment, 1180 may include an illumination source 1182 for illuminating the GI tract, and an imaging sensor 1184 for capturing images of areas of the GI tract illuminated by illumination source 1182. Imaging part, section, or compartment, 1180 may also include a controller for controlling operation of illumination source 1182 and imaging sensor 1184. The controller may also control the operation of cam 1140, and, in general, the operation mode of the cytology part of capsule 1100.

FIG. 12 shows a partial cross-section view of a cytology capsule 1200 according to another example embodiment. Cytology capsule 1200 may include a rotatable (dynamic) sampling wheel 1210 that may reside in a leak proof chamber 1250. Cytology capsule 1200 may also include a motor (the motor, which may be, for example, an off-the-shelf piezoelectric motor of Nanomotion Ltd., an Israeli company, is not shown in FIG. 12). Sampling wheel 1210 may be rotated about axis 1230 by the motor (and in some embodiments by using also a gear mechanism), for example in the counter clockwise direction 1240. Sampling wheel 1210 may include a plurality of sampling cavities, similar to sampling cavity 1250, on its circumference. Each circumferential sampling cavity may include a cavity and a porous or absorbing material (e.g., sponge, sponge-like material, etc.) that is contained in the cavity. In general, the porous or absorbing material in each cavity may be adapted to absorb various body fluids and/or to scrape cells off a body tissue. Cavity 1220 is shown empty for the sake of clarity, while the other cavities are shown containing a porous material (for example, sampling cavity 1250 is shown containing porous material 1252). Since different body fluids may have different properties (e.g., viscosity, acidity, etc.), the porous material in the sampling cavities may be made of different materials and/or with different porosities to accommodate for different body samples and/or fluids.

Figure 13:
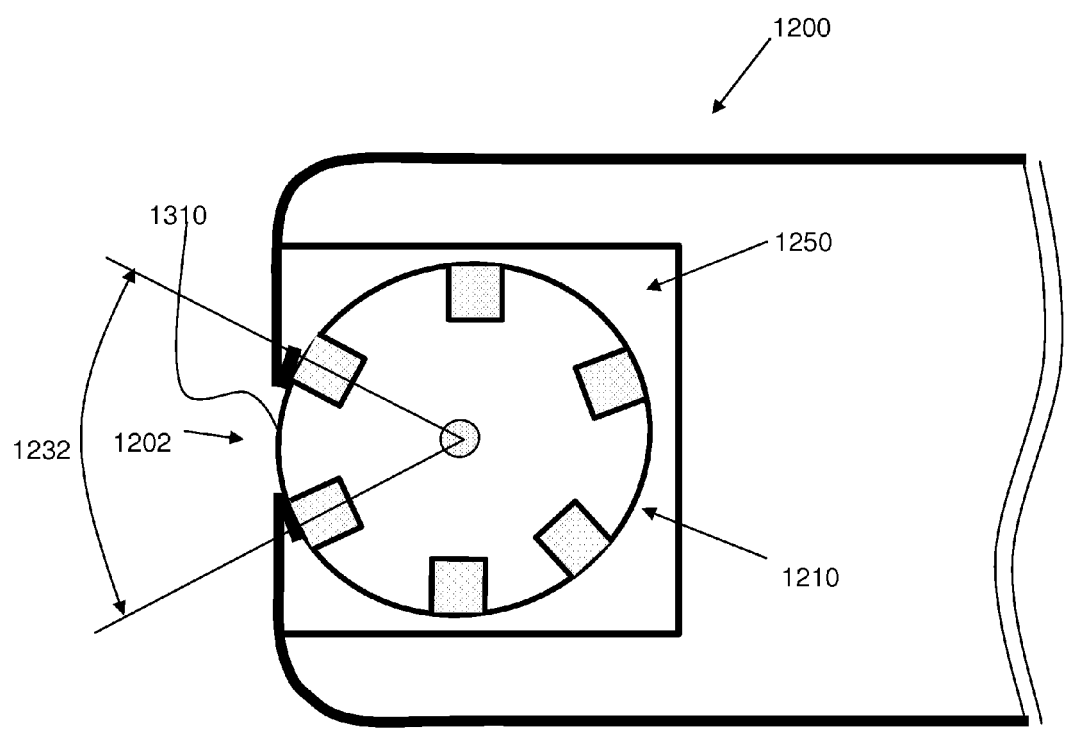
FIG. 13 shows a partial cross-section view of a cytology capsule according to yet another example embodiment.

Sampling wheel 1210 may be rotated in a stepwise manner corresponding, for example, to a predefined sampling plan or scheme. For example, at each step, sampling wheel 1210 may be rotated a predefined amount of degrees corresponding, for example, to a basic angle 1232. Basic angle 1232 may be contingent on the number (s) of circumferential sampling cavities, for example basic angle 1232 may be equal to 360/s degrees. By way of example, FIG. 12 shows eight sampling cavities (s=8), and angle 1232 may be equal to 360/8=45 degrees. In another example, at each step, sampling wheel 1210 may be rotated a predefined amount of degrees corresponding, for example, to n times (n>1, e.g., n may equal to 2, 3, etc.) that angle (e.g., n times basic angle 1232). Currently, porous material 1221 is shown facing porthole window 1202, through which it may scrape cells off a tissue, or absorb a body fluid. Assume that capsule 1200 is in a specific location of interest in the GI system and n=2 for that particular location. In response to a command to rotate sampling wheel 1210 under the above mentioned constraints (specific GI location and n=2), sampling wheel 1210 turns 90 (2×45) degrees CCW and, while it revolves, porous material 1222 goes past porthole window 1202 (while scraping cells off a tissue or absorbing body fluids, as the case may be), and then porous material 1223 takes the place of porous material 1222 against porthole window 1202. Since the sampling wheel is brought to a stop position after it revolves 90 degrees (as per the example), porous material 1223 remains facing porthole window 1202 until a next command is issued (externally to capsule 1200, or internally) to rotate sampling wheel 1210 further. Referring also to FIG. 13, sampling wheel 1210, porthole window 1202, and angle 1232 may be configured such that when sampling wheel 1210 completes an operation revolution (e.g., after all the sampling cavities have been used), the sampling wheel may be rotated further such that outer surface 1310 of sampling wheel 1210 tightly seals chamber 1250. Alternatively, the sampling wheel may be brought to a resting position in which the outer surface 1310 of sampling wheel 1210 tightly seals chamber 1250 after each rotation step. The outer surface of the sampling wheel may be made of a bacteriostatic coating to prevent contamination between sampling cavities. The gasket between the porthole window and the sampling wheel may also be made of bacteria-deterring material.

Figure 14:
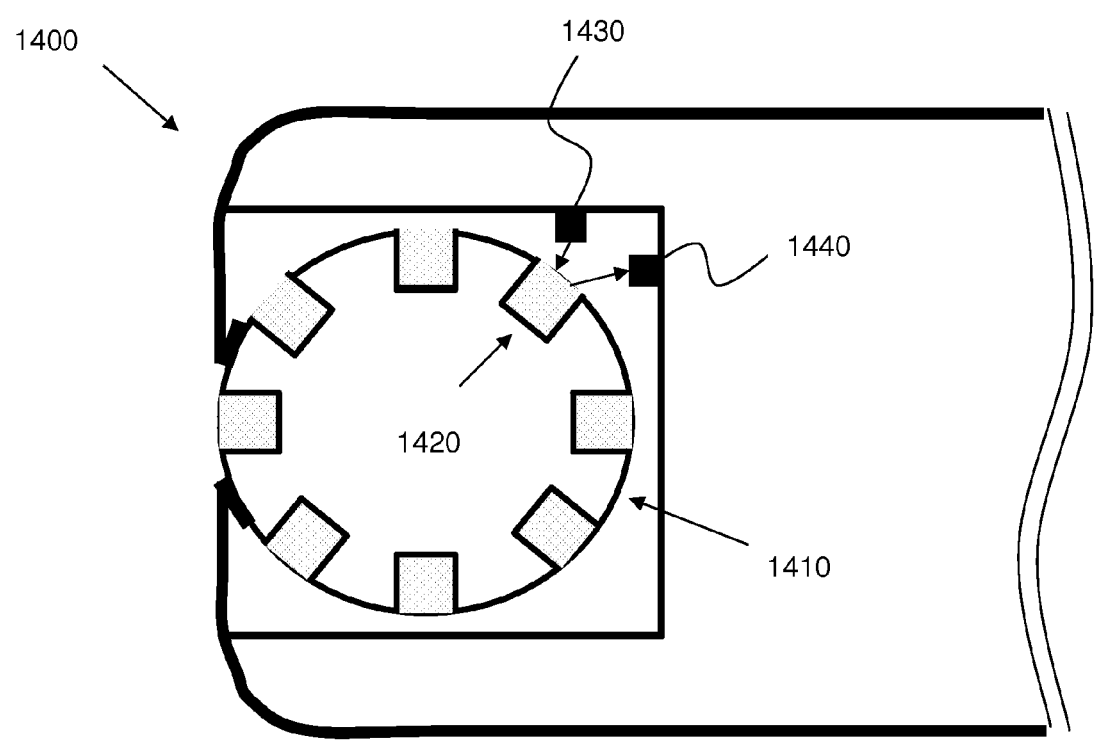
FIG. 14 shows a cytology capsule according to another example embodiment.

FIG. 14 shows a cytology capsule 1400 according to another example embodiment. Capsule 1400 may be similar to cytology capsule 1200. Sampling wheel 1410, an example dynamic sampling wheel, may have multiple sampling cavities that may be similar to sampling cavity 1420. Capsule 1400 may also include an on-board cytology analysis system. The on-board cytology analysis system may include an excitation or stimulation source 1430, a detector 1440, and a controller for controlling the excitement/stimulation source 1430, and for processing or interpreting the output of detector 1440. Each of the sampling cavities (e.g., sampling cavity 1420) may be soaked in a bio-sense or bio-marker agent so that when the agent contacts a certain type of tissue cells or body fluid, the cells, or fluid, may emit a visible light when exposed to an electromagnetic radiation, for example to an Ultraviolet light. Thus, detection of a visible light emitted from cells or fluid may enable the controller to detect the presence of the cells or body fluid.

Sampling cavity 1420 is shown in a test position, in which the tissue cells or body fluid scraped off or absorbed by the porous material of sampling cavity 1420 (and interact with the bio-sense or bio-marker agent) may be tested. During the test process, the sample in the sampling cavity 1420 is excited or stimulated by the excitation/stimulation source. The excitation/stimulation source may emit, for example, an Ultraviolet light onto the sample cells/fluid, and detector 1440 may detect the consequent visible light.

As explained above, for example, in connection with FIG. 12, a particular sampling cavity may be used to sample tissue cells or fluid in a particular location in the GI system. Therefore, after the sample content of a particular sampling cavity is tested in the way described above, it may be beneficial to associate the test results obtained for the particular sampling cavity with the particular location in the GI system.

In some embodiments some of the sampling cavities of a sampling wheel may be dedicated to a particular type of tissue cells, pathogen cells, or fluid(s) while other sampling cavities of the sampling wheel may be dedicated to other types of tissue cells, pathogen cells, or fluid(s). In another embodiment, a capsule may contain more than one sampling wheel (e.g., two sampling wheels), and each sampling wheel may be dedicated to different tissue cells, pathogen cells, or fluid(s). The sampling wheels may be adjacent to each other, and they may be controlled individually. For example, when a first sampling wheel is exhausted (fully used), another sampling wheel may be used, and so on. Using multiple sampling wheels enables increasing the total number of sampling cavities in a capsule. Sampling wheels such as, for example, sampling wheels 1110, 1210, 1310, and 1410, may replace sharp protruding tools such as needles, injectors and other sharp objects that may injure or tangle with, for example, tissues.

In order to use the cytology capsule efficiently (for example to ensure tissue cells and/or body fluids are taken from desired locations), a maneuvering module may be added to the capsule. Such a module may include permanent magnet(s) and eddy current manifold that are respectively sensitive to external direct current ("DC") electromagnetic field and alternating current ("AC") electromagnetic field. The external electromagnetic fields may exert force on the permanent magnets and on the eddy current manifold to thereby steer the cytology capsule to the desired locations, and to orient the capsule to the desired directions. The cytology capsule may also contain localization means sensitive to an external localization system. The localization means may include one or more electromagnetic field sensing coils, and the external localization system may generate an electromagnetic signal that may be sensed by the electromagnetic field sensing coils. The localization means and the localization system may facilitate determination, in real-time, of the location and orientation of the capsule, and consequent real-time localization data may be provided to the external system applying the external maneuvering forces on the capsule, in order to accurately maneuver the cytology capsule. Since magnetic maneuvering involves applying a magnetic force on permanent magnets in the maneuvered capsule, operating a sampling wheel by a driving mechanism that is unaffected by magnetic fields (e.g., a spring, as demonstrated by FIG. 11, or a motor, as explained, for example, in connection with FIG. 12) is preferable. An example of a maneuverable capsule and of a maneuvering system may be found in a U.S. patent application Ser. No. 12/963,502, entitled "MAGNETICALLY MANEUVERABLE IN-VIVO DEVICE".

Due to strict space constraints (swallowable capsules have to be small enough for ingestion), adding maneuvering components (e.g., permanent magnets, eddy current manifold, sensing coils) to the capsule does not leave much space for a sampling wheel (or drum). Therefore, adding a sampling wheel or drum to a magnetically maneuvered capsule requires that various capsule's components, including the permanent magnets, eddy current manifold, sensing coils and the sampling wheel or drum, be meticulously designed, so that they can coexist both physically and operationally.

Figure 15:
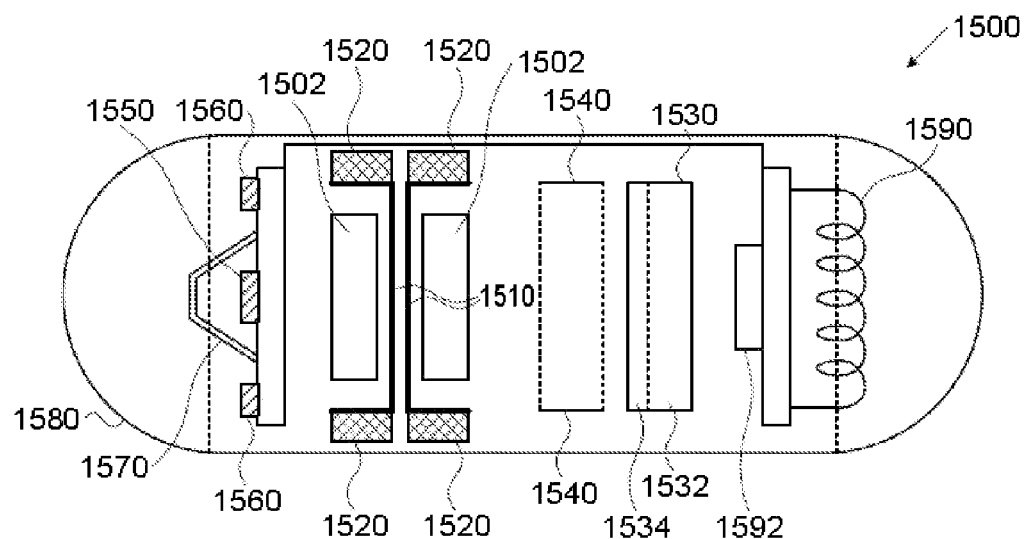
FIG. 15 shows a magnetically maneuverable cytology in-vivo capsule according to an example embodiment.

FIG. 15 shows a magnetically maneuverable cytology in-vivo capsule 1500 according to an example embodiment. Capsule 1500 may include batteries 1502, cylindrically shaped permanent magnets 1520 to transform an external electromagnetic field into a maneuvering force to steer capsule 1500, eddy current manifold 1510 to restrain the movement of capsule 1500, cylindrically shaped electromagnetic field sensing coil(s) 1540 to sense localization signals, image sensor 1550 for capturing images of the GI system, illumination source 1560 for illuminating the GI system, optical head 1570, visually transparent dome 1580, transmitter 1590 for transmitting the images captured by image sensor 1550, sampling (cytology) module 1530, and controller 1592 for controlling operation of capsule 1500. Sampling module 1530 may include a sampling portion 1532 that may include a drum and a brush or sampling wheel that may be similar to any of the drum/brush/sampling wheels described above, and a driving mechanism 1534 that may be similar to any of the driving mechanism described above.

Figure 16:
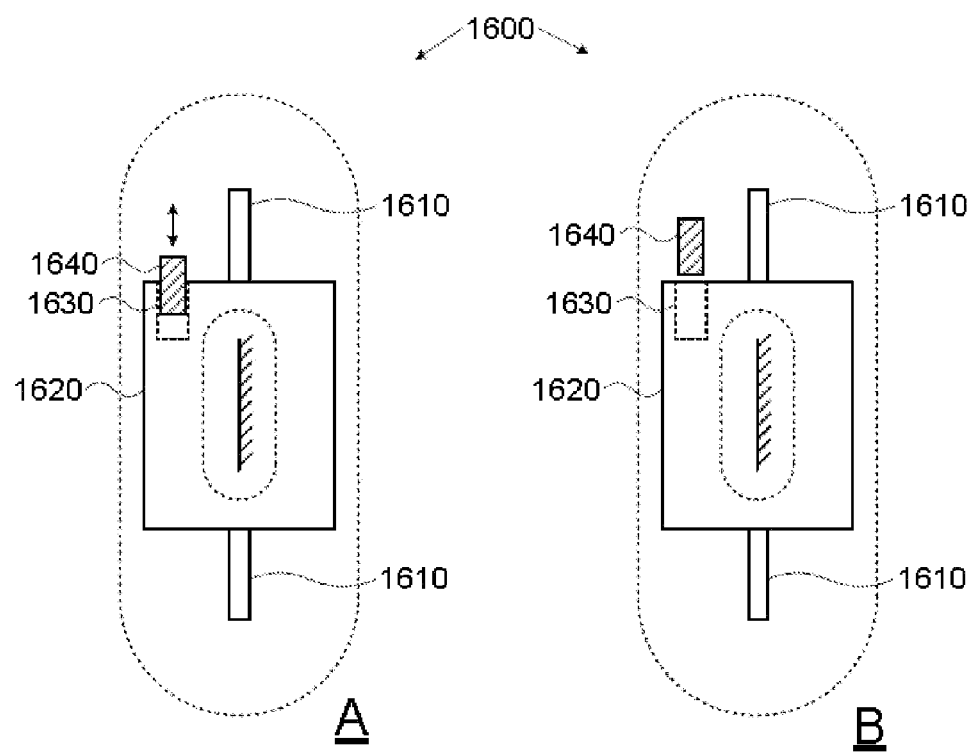
FIG. 16 shows a cytology capsule with an example locking/unlocking mechanism according to another example embodiment.

FIG. 16 shows a cytology capsule 1600 with an example locking/unlocking mechanism according to another example embodiment. Cytology capsule 1600 may include a drum 1620, which may be similar to any of the drums described above, and other components which are not shown in FIG. 16 (e.g., an image sensor, a transceiver, a controller, a maneuvering module, etc.). Drum 1620 may include a recess 1630 to facilitate locking and unlocking drum 1620. In order to lock drum 1620 (to inhibit inadvertent rotation thereof), a pin 1640 is pushed into recess 1630. In order to unlock drum 1620 (to enable it to rotate), pin 1640 is pulled out of recess 1630. Pin 1640 may be pushed in and pulled out by using, for example, a solenoid mechanism or a motor. When pin 1640 is pulled out of recess 1630, drum 1620 may rotate about axle 1610.

Figure 17:
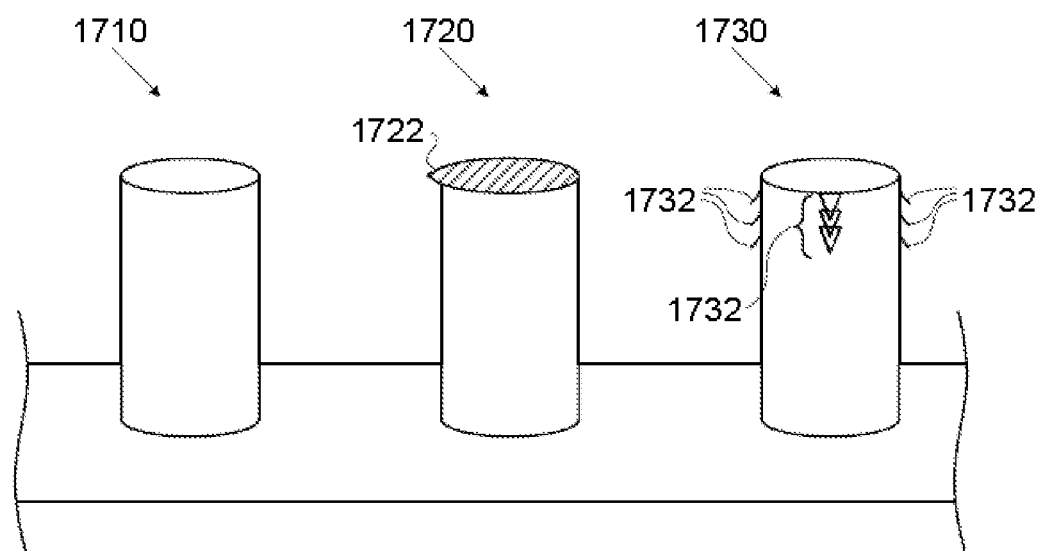
FIG. 17 shows brush bristles according to some example embodiments.

FIG. 17 shows brush bristles according to some example embodiments. Brush bristle 1710 is a plain bristle; brush bristle 1720 includes a miniature adze-like cutting surface 1722, and brush bristle 1730 includes small spikes 1732 on the tip of the bristle to improve gathering and adherence to tissue cells. A brush used by a cytology capsule may include any combination of brush bristles similar to 1710, brush bristles similar to brush bristle 1720, and brush bristles similar to brush bristle 1730. Alternatively or additionally, other types of bristles may be used.

It will be appreciated that the present invention is not limited to what has been particularly shown and described hereinabove. Rather the scope of the present invention is defined only by the claims which follow.

What is claimed is:

1. A swallowable capsule for in-vivo cytology acquisition comprising:
   a capsule housing;
   at least one rotatable drum having a body and being rotatably mounted about a spindle within said capsule housing so as to be rotatable relative thereto, said rotatable drum comprising a sampling cavity defined by the body of the rotatable drum and having an opening in the body and into said sampling cavity;
   a brush attached onto said drum within said sampling cavity for brushing against a tissue and acquiring cytology; and
   a porthole in said housing through which the brush may make contact with the tissue;
   wherein rotating said rotatable drum relative to said housing either aligns said opening with said porthole to acquire cytology using the brush or aligns a portion of said body with said porthole to seal said sampling cavity from an environment external to said housing.

2. The capsule according to claim 1, wherein the capsule further comprises a magnet attached to said drum.

3. The capsule according to claim 1, wherein the capsule is operated remotely without requiring wires or attachments passing through the mouth or anus.

4. The capsule according to claim 1, wherein the capsule is attached to a thread or wire to operate the brush or to provide power and commands to the capsule.

5. The capsule according to claim 1, wherein the drum comprises a fixative or preservative substance to prevent the cytology from degrading or decaying.

6. The capsule according to claim 1, wherein the brush includes bristles modified to scrape off and to retain cells.

7. The capsule according to claim 1, wherein the capsule comprises:
a plurality of rotatable drums, brushes and portholes, wherein each rotatable drum has attached thereto a respective brush for sampling any of tissue cells and body fluids through a respective porthole.

8. The capsule as in claim 1, wherein the capsule comprises a sampling wheel, wherein said sampling wheel comprises the at least one rotatable drum mounted thereto and is either of a static sampling wheel and a dynamic sampling wheel.

9. The capsule as in claim 8, wherein the static sampling wheel comprises on-board portholes.

10. The capsule as in claim 1, wherein the drum is rotatable using any of: a spring, a motor, a magnet, and an external electromagnetic field.

11. The capsule as in claim 1, further comprising permanent magnets to facilitate electromagnetic maneuvering of the capsule by an external electromagnetic field.

12. The capsule as in claim 7, wherein the drum comprises a locking/unlocking recess adapted to accept a locking cam or locking pin.

13. The capsule as in claim 7, wherein the external surface of the drum comprises a bacteriostatic layer.

14. A system for in-vivo cytology acquisition comprising:
a swallowable capsule comprising:
 a capsule housing;
 at least one rotatable drum having a body and being rotatably mounted about a spindle within said capsule housing so as to be rotatable relative thereto, said rotatable drum having attached thereon an internal magnet and comprising a sampling cavity defined by the body of the rotatable drum and having an opening in the body and into said sampling cavity;
 a brush attached to said drum within said sampling cavity for brushing against a tissue and acquiring cytology; and
 a porthole in said housing through which the brush may be in contact with the tissue; and
 a rotatable external magnet for rotating the internal magnet and thereby rotating the drum and brush;
wherein rotating said rotatable drum relative to said housing either aligns said opening with said porthole to acquire cytology using the brush or aligns a portion of said body with said porthole to seal said sampling cavity from an environment external to said housing.

15. A method for in-vivo cytology acquisition comprising:
inserting into a patient a swallowable cytology capsule, said capsule comprising a capsule housing having at least one rotatable drum rotatably having a body and being mounted about a spindle within said capsule housing so as to be rotatable relative thereto and having an opening in the body and into said sampling cavity, said rotatable drum having attached thereon an internal magnet and comprising a sampling cavity defined by the body of the rotatable drum, a brush attached onto said rotatable drum within said sampling cavity for brushing against a tissue and acquiring cytology, and a porthole in said housing through which the brush may be in contact with the tissue, wherein rotating said rotatable drum relative to said housing either aligns said opening with said porthole to acquire cytology using the brush or aligns a portion of said body with said porthole to seal said sampling cavity from an environment external to said housing;
rotating an external magnet in close proximity to the patient, thereby rotating said brush against a tissue; and
acquiring cytology from said tissue using the brush.

* * * * *